US012632773B2

(12) United States Patent
Jiang et al.

(10) Patent No.: US 12,632,773 B2
(45) Date of Patent: May 19, 2026

(54) INSULIN THERAPY DETERMINATION

(71) Applicant: Medtronic MiniMed, Inc., Northridge, CA (US)

(72) Inventors: Boyi Jiang, Pasadena, CA (US); Yuxiang Zhong, Arcadia, CA (US); Pratik J. Agrawal, Porter Ranch, CA (US); Ali Dianaty, Porter Ranch, CA (US)

(73) Assignee: MEDTRONIC MINIMED, INC., Northridge (CA)

( * ) Notice: Subject to any disclaimer, the term of this patent is extended or adjusted under 35 U.S.C. 154(b) by 979 days.

(21) Appl. No.: 17/162,091

(22) Filed: Jan. 29, 2021

(65) Prior Publication Data

US 2022/0245504 A1 Aug. 4, 2022

(51) Int. Cl.
| | |
|---|---|
| *G06N 20/00* | (2019.01) |
| *G16B 40/20* | (2019.01) |
| *G16H 10/60* | (2018.01) |
| *G16H 20/60* | (2018.01) |

(52) U.S. Cl.
CPC ............. *G06N 20/00* (2019.01); *G16B 40/20* (2019.02); *G16H 10/60* (2018.01); *G16H 20/60* (2018.01)

(58) Field of Classification Search
CPC ........ G06N 20/00; G16B 40/20; G16H 10/60; G16H 20/60; G16H 50/50; G16H 20/17; A61M 5/14248; A61M 2005/14208; A61M 2005/14252; A61M 2205/33; A61M 2230/201; A61B 5/14503; A61B 5/14532
See application file for complete search history.

(56) References Cited

U.S. PATENT DOCUMENTS

| | | | |
|---|---|---|---|
| 2011/0098548 A1* | 4/2011 | Budiman | G16H 50/50 600/365 |
| 2015/0227710 A1* | 8/2015 | Pappada | G16H 70/20 705/2 |
| 2018/0271455 A1 | 9/2018 | Zhong et al. | |
| 2019/0246973 A1* | 8/2019 | Constantin | A61B 5/7221 |
| 2019/0321553 A1* | 10/2019 | Grosman | A61B 5/4839 |
| 2020/0016336 A1 | 1/2020 | Patek et al. | |
| 2020/0135320 A1 | 4/2020 | Meugels | |
| 2023/0197237 A1* | 6/2023 | Mensinger | A61M 5/31553 705/3 |

OTHER PUBLICATIONS

Extended Search Report from counterpart European Application No. 22153647.7 dated Jun. 23, 2022, 12 pp.

(Continued)

*Primary Examiner* — Jason B Dunham

*Assistant Examiner* — Amanda R. Covington

(74) *Attorney, Agent, or Firm* — Weaver Austin Villeneuve & Sampson LLP

(57) ABSTRACT

Techniques for determining insulin therapy are described. The techniques include obtaining patient characteristic information for a current patient; determining, with a machine-learning model, an insulin delivery therapy from a plurality of insulin delivery therapies for the current patient based on the patient characteristic information, wherein the machine-learning model is generated based on digital representations of a plurality of patients; and outputting information indicative of the determined insulin delivery therapy.

20 Claims, 7 Drawing Sheets

(56)     References Cited

OTHER PUBLICATIONS

Response to Extended Search Report dated Aug. 8, 2022, from counterpart European Application No. 22153647.7 filed Jan. 26, 2023, 14 pp.
IEEE 802.11ad, "IEEE Standard for Information Technology—Telecommunications and Information Exchange Between Systems—Local and Metropolitan Area Networks—Specific Requirements—Part 11: Wireless LAN Medium Access Control (MAC) and Physical Layer (PHY) Specifications—Amendment 3: Enhancements for Very High Throughput in the 60 GHz Band", IEEE Computer Society, Dec. 28, 2012, 628 pp. IEEE 802.11ad, "IEEE Standard for Information Technology—Telecommunications and Information Exchange Between Systems—Local and metropolitan area networks—Specific requirements".
Brazeau et al., "Carbohydrate counting accuracy and blood glucose variability in adults with type 1 diabetes," Diabetes Research and Clinical Practice, vol. 99, No. 1, Jan. 2013, 5 pp.
Jiang, B., "Estimating an Optimal Meal Bolus For Person with Diabetes on Multiple Daily Injections Therapy without Carb Counting," American Diabetes Association 80th Scientific Sessions, Jun. 12-16, 2020, 9 pp.
Reiterer et al., "Impact of Carbohydrate Counting Errors on Glycemic Control in Type 1 Diabetes," IFAC—PapersOnLine, vol. 51, No. 27, Dec. 2018, 6 pp.
EP Office Action dated Feb. 9, 2024 in EP Application No. 22153647.7.
CN Office Action dated Mar. 17, 2026 in CN Application No. 202210076492.7, with English Translation.

* cited by examiner

CLOUD
26

ML MODEL
34

DIGITAL REPRESENTATIONS
32

DATABASE
30

PROCESSOR
28A

● ●

PROCESSOR
28N

10C

12

20

PHYSICIAN DEVICE
36

PATIENT DEVICE
24

INJECTION DEVICE
40

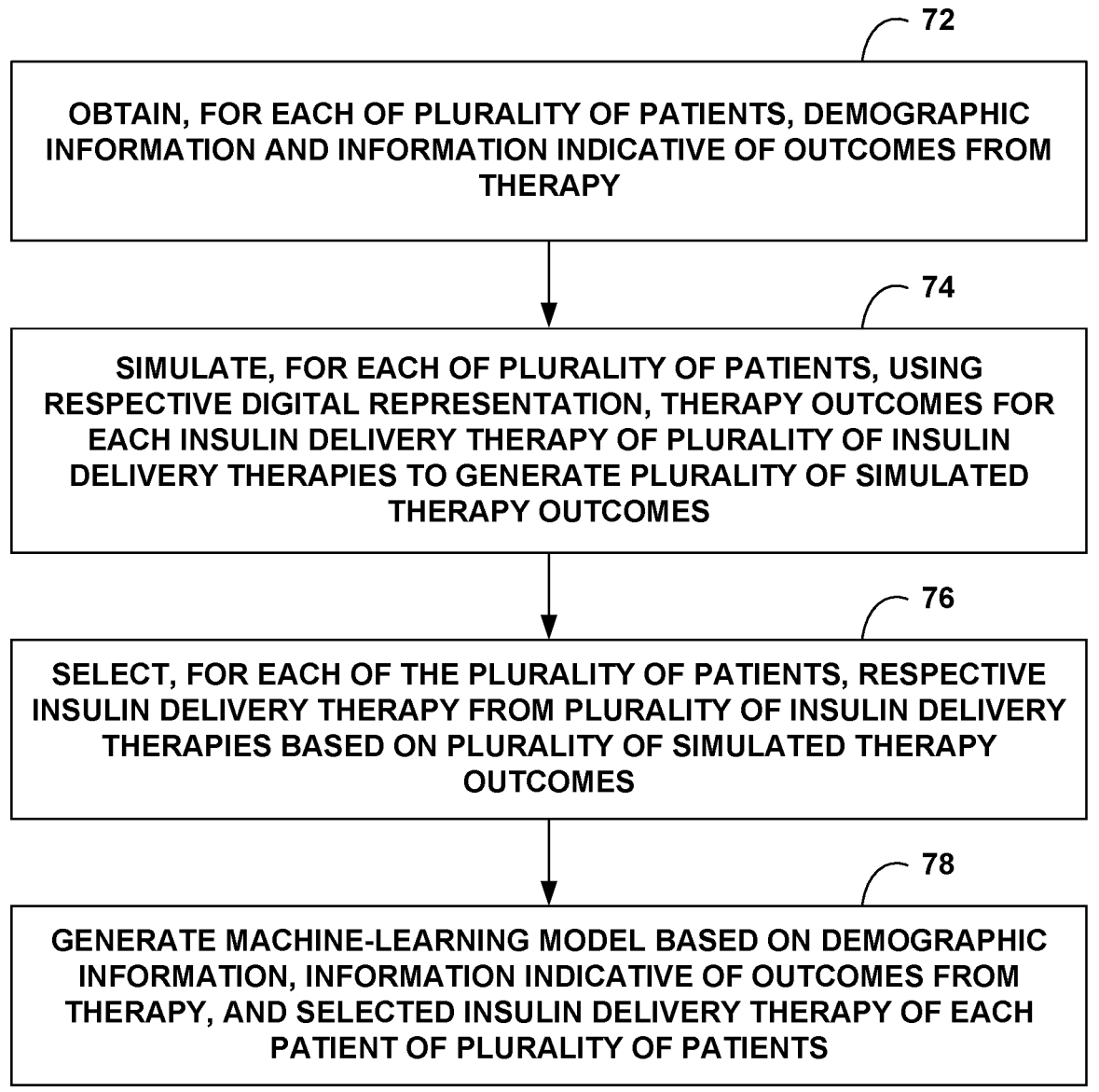

72

OBTAIN, FOR EACH OF PLURALITY OF PATIENTS, DEMOGRAPHIC INFORMATION AND INFORMATION INDICATIVE OF OUTCOMES FROM THERAPY

74

SIMULATE, FOR EACH OF PLURALITY OF PATIENTS, USING RESPECTIVE DIGITAL REPRESENTATION, THERAPY OUTCOMES FOR EACH INSULIN DELIVERY THERAPY OF PLURALITY OF INSULIN DELIVERY THERAPIES TO GENERATE PLURALITY OF SIMULATED THERAPY OUTCOMES

76

SELECT, FOR EACH OF THE PLURALITY OF PATIENTS, RESPECTIVE INSULIN DELIVERY THERAPY FROM PLURALITY OF INSULIN DELIVERY THERAPIES BASED ON PLURALITY OF SIMULATED THERAPY OUTCOMES

78

GENERATE MACHINE-LEARNING MODEL BASED ON DEMOGRAPHIC INFORMATION, INFORMATION INDICATIVE OF OUTCOMES FROM THERAPY, AND SELECTED INSULIN DELIVERY THERAPY OF EACH PATIENT OF PLURALITY OF PATIENTS

FIG. 7

INSULIN THERAPY DETERMINATION

TECHNICAL FIELD

The disclosure relates to medical systems and, more particularly, to medical systems for therapy for diabetes.

BACKGROUND

A patient with diabetes typically receives insulin from an insulin delivery device (e.g., a pump or injection device) to control the glucose level in his or her bloodstream. Naturally produced insulin may not control the glucose level in the bloodstream of a diabetes patient due to insufficient production of insulin and/or due to insulin resistance. To control the glucose level, a patient's therapy routine may include basal dosages and bolus dosages of insulin. Basal dosages tend to keep glucose levels at consistent levels during periods of fasting. Bolus dosages may be delivered to the patient specifically at or near mealtimes or other times where there may be a relatively fast change in glucose level.

SUMMARY

Disclosed herein are techniques for insulin therapy determination. The techniques may be practiced using systems; processor-implemented methods; and non-transitory processor-readable storage media storing instructions which, when executed by one or more processors, cause performance of the techniques.

In some examples, the techniques may involve obtaining patient characteristic information for a current patient; determining, with a machine-learning model, an insulin delivery therapy from a plurality of insulin delivery therapies for the current patient based on the patient characteristic information, wherein the machine-learning model is generated based on digital representations of a plurality of patients; and outputting information indicative of the determined insulin delivery therapy.

The details of one or more aspects of the disclosure are set forth in the accompanying drawings and the description below. Other features, objects, and advantages of this disclosure will be apparent from the description and drawings, and from the claims.

BRIEF DESCRIPTION OF DRAWINGS

FIG. 7 is a flowchart illustrating an example process for generating a machine learning model for insulin therapy determination.

DETAILED DESCRIPTION

Devices, systems, and techniques for insulin therapy determination are described in this disclosure. For diabetics, changes in glucose levels, such as increases in glucose levels, may be controlled with supplemental insulin. For instance, diabetics tend to be resistant to insulin or fail to produce sufficient insulin to reduce glucose levels. Thus, they may rely on delivery of supplemental insulin in bolus and/or basal dosages to keep glucose levels within a target range (e.g., within 100 dl/mg to 180 dl/mg) having an upper limit that is a predetermined number of values below a hyperglycemic glucose level and a lower limit that is a predetermined number of values above a hypoglycemic glucose level.

However, different patients may have different insulin delivery therapies. This may be at least partly due to different patients having different preferences, which can affect therapy adherence. For example, a first therapy may correspond to delivery of the same amount of insulin after each meal, and a second therapy may correspond to a customized amount of insulin (e.g., different amounts of insulin) for each meal. In theory, the second therapy should provide a better clinical outcome (e.g., glucose levels maintained within a target range for a longer period of time) than the first therapy, but in reality, patient preference may cause the second therapy to result in a poorer clinical outcome than what would have resulted from the first therapy. For example, the second therapy may involve carbohydrate counting, but a patient who prefers simplicity over accuracy may use random values instead of taking the time to find out the carbohydrate content of a meal. For such a patient, uniform amounts of insulin for each meal could have resulted in a better clinical outcome than customized amounts of insulin for each meal.

This disclosure describes example techniques for determining an insulin delivery therapy for a current patient in a manner that balances clinical outcome with patient preference. This may be achieved based on generating a machine learning model that correlates patient characteristics (e.g., demographic information) with the insulin delivery therapy that corresponds to the best clinical outcome for a patient with those characteristics. Thus, the model can be used to predict the insulin delivery therapy that will provide the best clinical outcome for the current patient based on the current patient's characteristics.

It should be appreciated that the techniques disclosed herein can be practiced with one or more types of insulin (e.g., fast-acting insulin, intermediate-acting insulin, and/or slow-acting insulin). Thus, terms such as "basal insulin" and "bolus insulin" do not necessarily denote different types of insulin. For example, fast-acting insulin may be used for both basal dosages and bolus dosages.

Figure 1:
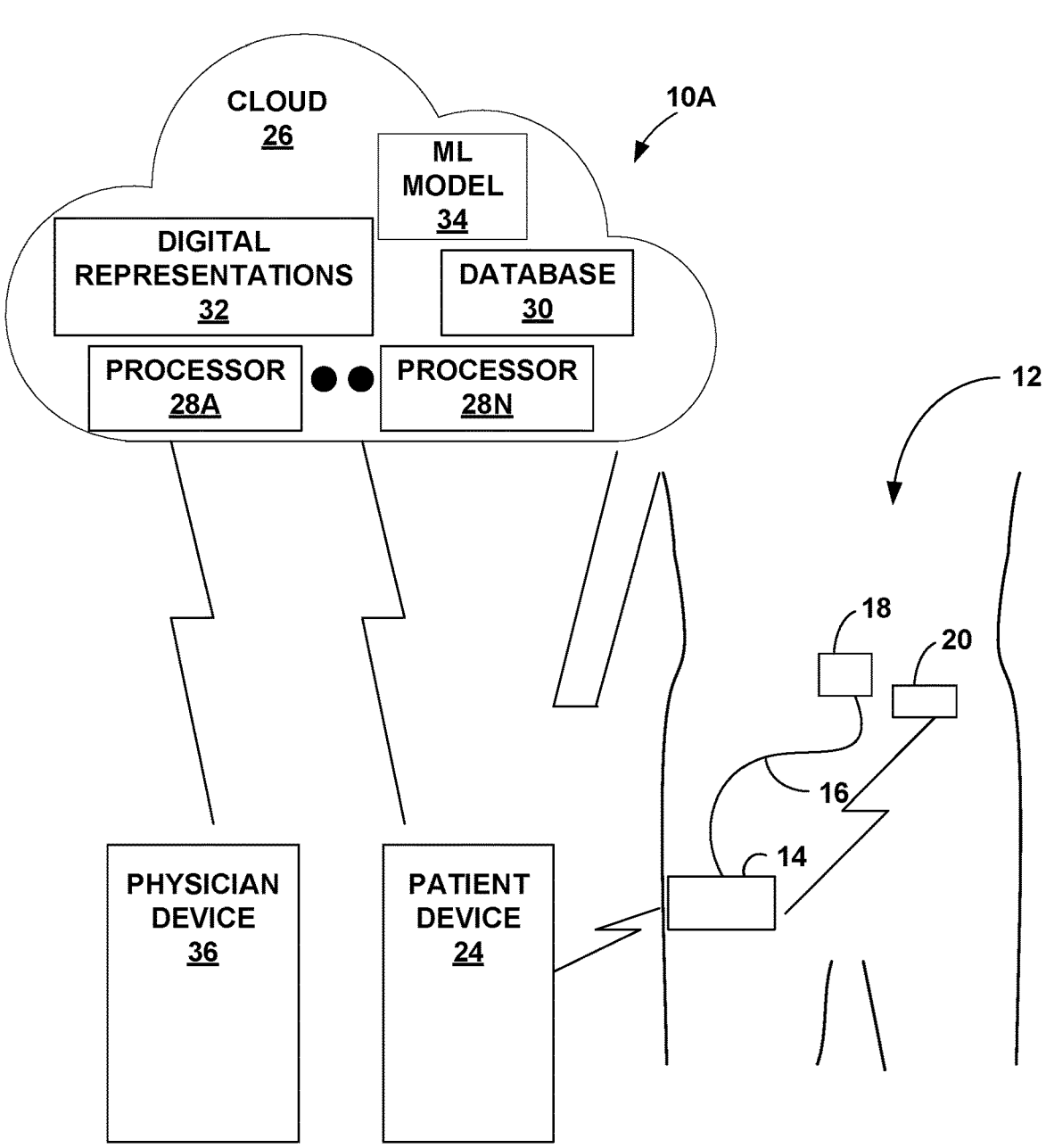
FIG. 1 is a block diagram illustrating an example insulin therapy determination system comprising an insulin pump, in accordance with one or more examples described in this disclosure.

FIG. 1 is a block diagram illustrating an example insulin therapy determination system comprising an insulin pump, in accordance with one or more examples described in this disclosure. FIG. 1 illustrates system 10A that includes insulin pump 14, tubing 16, infusion set 18, monitoring device 20 (e.g., a glucose level monitoring device), patient device 24, cloud 26, and physician device 36. Cloud 26 represents a local, wide area or global computing network including one or more processors 28A-28N ("one or more processors 28") that are within one or more network devices (e.g., one network device may include one or more processors 28 or one or more processors 28 may be distributed across a plurality of network devices). In some examples, the various components may determine changes to therapy based on determination of glucose level by monitoring device 20, and therefore system 10A may be referred to as glucose level management system 10A.

Patient 12 may be diabetic (e.g., Type 1 diabetic or Type 2 diabetic), and therefore, the glucose level in patient 12 may be controlled with delivery of supplemental insulin. For example, patient 12 may not produce sufficient insulin to control the glucose level or the amount of insulin that patient 12 produces may not be sufficient due to insulin resistance that patient 12 may have developed.

To receive the supplemental insulin, patient 12 may carry insulin pump 14 that couples to tubing 16 for delivery of insulin into patient 12. Infusion set 18 may connect to the skin of patient 12 and include a cannula to deliver insulin into patient 12. Monitoring device 20 may also be coupled to patient 12 to measure glucose level in patient 12. Insulin pump 14, tubing 16, infusion set 18, and monitoring device 20 may together form an insulin pump system. One example of the insulin pump system is the MINIMED™ 670G insulin pump system by MEDTRONIC MINIMED, INC. However, other examples of insulin pump systems may be used and the example techniques should not be considered limited to the MINIMED™ 670G insulin pump system. For example, the techniques described in this disclosure may be utilized in insulin pump systems that include wireless communication capabilities. However, the example techniques should not be considered limited to insulin pump systems with wireless communication capabilities, and other types of communication, such as wired communication, may be possible. In another example, insulin pump 14, tubing 16, infusion set 18, and/or monitoring device 20 may be contained in the same housing.

Insulin pump 14 may be a relatively small device that patient 12 can place in different locations. For instance, patient 12 may clip insulin pump 14 to the waistband of pants worn by patient 12. In some examples, to be discreet, patient 12 may place insulin pump 14 in a pocket. In general, insulin pump 14 can be worn in various places, and patient 12 may place insulin pump 14 in a location based on the particular clothes patient 12 is wearing.

To deliver insulin, insulin pump 14 includes one or more reservoirs (e.g., two reservoirs). A reservoir may be a plastic cartridge that holds up to N units of insulin (e.g., up to 300 units of insulin) and is locked into insulin pump 14. Insulin pump 14 may be a battery-powered device that is powered by replaceable and/or rechargeable batteries.

Tubing 16 may connect at a first end to a reservoir in insulin pump 14 and may connect at a second end to infusion set 18. Tubing 16 may carry the insulin from the reservoir of insulin pump 14 to patient 12. Tubing 16 may be flexible, allowing for looping or bends to minimize concern of tubing 16 becoming detached from insulin pump 14 or infusion set 18 or concern of tubing 16 breaking.

Infusion set 18 may include a thin cannula that patient 12 inserts into a layer of fat under the skin (e.g., subcutaneous connection). Infusion set 18 may rest near the stomach of patient 12. The insulin may travel from the reservoir of insulin pump 14, through tubing 16, through the cannula in infusion set 18, and into patient 12. In some examples, patient 12 may utilize an infusion set insertion device. Patient 12 may place infusion set 18 into the infusion set insertion device, and with a push of a button on the infusion set insertion device, the infusion set insertion device may insert the cannula of infusion set 18 into the layer of fat of patient 12, and infusion set 18 may rest on top of the skin of the patient with the cannula inserted into the layer of fat of patient 12.

In some examples, insulin pump 14 may be an implantable insulin pump. For ease of description, the disclosure is described with respect to insulin pump 14 being external to patient 12.

Monitoring device 20 may include a glucose sensor that is inserted under the skin of patient 12, such as near the stomach of patient 12 or in the arm of patient 12 (e.g., subcutaneous connection). Monitoring device 20 may be configured to measure the interstitial glucose level, which is the glucose found in the fluid between the cells of patient 12. Monitoring device 20 may be configured to continuously or periodically sample the glucose level and rate of change of the glucose level over time.

In one or more examples, insulin pump 14, monitoring device 20, and/or the various components illustrated in FIG. 1, may together form a closed-loop therapy delivery system. For example, patient 12 may set a target glucose level, usually measured in units of milligrams per deciliter, on insulin pump 14. Insulin pump 14 may receive the current glucose level from monitoring device 20 and, in response, may increase or decrease the amount of insulin delivered to patient 12 (e.g., by delivering a varying number of discrete boluses of insulin or changing the bolus size of insulin). For example, if the current glucose level is higher than the target glucose level, insulin pump 14 may increase the insulin. If the current glucose level is lower than the target glucose level, insulin pump 14 may temporarily cease delivery of the insulin. Insulin pump 14 may be considered as an example of an automated insulin delivery (AID) device. Other examples of AID devices may be possible, and the techniques described in this disclosure may be applicable to other AID devices.

Insulin pump 14 and monitoring device 20 may be configured to operate together to mimic some of the ways in which a healthy pancreas works. Insulin pump 14 may be configured to deliver basal dosages, which are small amounts of insulin released continuously or substantially continuously throughout the day. There may be times when glucose levels increase, such as due to eating or some other activity that patient 12 undertakes. Insulin pump 14 may be configured to deliver bolus dosages on demand in association with food intake or to correct an undesirably high glucose level in the bloodstream, e.g., supplementing the basal dosages. In one or more examples, if the glucose level rises above a target level, then insulin pump 14 may deliver a bolus dosage to address the increase in glucose level. Insulin pump 14 may be configured to compute basal and bolus dosages and deliver the basal and bolus dosages accordingly. For instance, insulin pump 14 may determine the amount of a basal dosage to deliver continuously and then determine the amount of a bolus dosage to deliver to reduce glucose level in response to an increase in glucose level due to eating or some other event. The term eating is used to generically refer to the act of consuming food and includes drinking as well.

Accordingly, in some examples, monitoring device 20 may sample glucose levels for determining rate of change in glucose level over time. Monitoring device 20 may output the glucose level to insulin pump 14 (e.g., through a wireless link connection like Bluetooth or BLE). Insulin pump 14 may compare the glucose level to a target glucose level (e.g., as set by patient 12 or a clinician) and adjust the insulin dosage based on the comparison.

As described above, patient 12 or a clinician may set one or more target glucose levels on insulin pump 14. There may be various ways in which patient 12 or the clinician may set a target glucose level on insulin pump 14. As one example, patient 12 or the clinician may utilize patient device 24 to communicate with insulin pump 14. A physician may utilize physician device 36 and/or patient device 24 to communicate with insulin pump 14.

Examples of patient device 24 and physician device 36 include mobile devices, such as smartphones, tablet computers, laptop computers, and the like. In some examples, patient device 24 and/or physician device 36 may be a special programmer or controller (e.g., a dedicated remote control device) for insulin pump 14. Although FIG. 1 illustrates one patient device 24, in some examples, there may be a plurality of patient devices. For instance, system 10A may include a mobile device and a dedicated wireless controller, each of which is an example of patient device 24. For ease of description only, the example techniques are described with respect to patient device 24 with the understanding that patient device 24 may be one or more patient devices.

Patient device 24 and/or physician device 36 may also be configured to interface with monitoring device 20. As one example, patient device 24 and/or physician device 36 may receive information from monitoring device 20 through insulin pump 14, where insulin pump 14 relays the information between patient device 24 and monitoring device 20. As another example, patient device 24 and/or physician device 36 may receive information (e.g., glucose level or rate of change of glucose level) directly from monitoring device 20 (e.g., through a wireless link).

In one or more examples, patient device 24 may comprise a user interface with which patient 12 or the clinician may control insulin pump 14. For example, patient device 24 may comprise a touchscreen that allows patient 12 or the clinician to enter a target glucose level. Additionally or alternatively, patient device 24 may comprise a display device that outputs the current and/or past glucose level. In some examples, patient device 24 may output notifications to patient 12, such as notifications if the glucose level is too high or too low, as well as notifications regarding any action that patient 12 needs to take. For example, if the batteries of insulin pump 14 are low on charge, then insulin pump 14 may output a low battery indication to patient device 24, and patient device 24 may in turn output a notification to patient 12 to replace or recharge the batteries.

Controlling insulin pump 14 through a display device of patient device 24 is merely provided as an example and should not be considered limiting. For example, insulin pump 14 may include pushbuttons that allow patient 12 or the clinician to set the various glucose levels of insulin pump 14. In some examples, insulin pump 14 itself, or in addition to patient device 24, may be configured to output notifications to patient 12. For instance, if the current, sensed glucose level is too high or too low, insulin pump 14 may output an audible or haptic output. In some examples, if the battery is low, then insulin pump 14 may output a low battery indication on a display of insulin pump 14.

As mentioned above, insulin pump 14 may deliver insulin to patient 12 based on current glucose levels (e.g., as measured by monitoring device 20). However, it should be appreciated that insulin delivery is not limited to implementations based on current glucose levels. For example, insulin pump 14 may deliver insulin to patient 12 based on a predicted glucose level (e.g., a future glucose level that is determined based on a glucose level trend).

In one or more examples, insulin pump 14 may be programmed with one or more insulin delivery therapies that define when and how much insulin to deliver. For example, the one or more insulin delivery therapies may define an amount of insulin to deliver after each meal. The amount of insulin to deliver may be the same for each meal, may be different for some meals, or may be different based on other information such as time of day, location, weekday or weekend, etc.

When a physician determines that patient 12 is to receive insulin therapy and prescribes use of insulin pump 14, the physician may determine an insulin delivery therapy with which to program insulin pump 14 so that insulin pump 14 can deliver therapy in accordance with the insulin delivery therapy. The physician may utilize his or her expertise to determine an insulin delivery therapy that is suitable for patient 12. For example, the physician may utilize physician device 36 to retrieve the patient record for patient 12 and may then determine insulin delivery therapy for patient 12 based on the patient record for patient 12.

In some examples, the physician may determine the insulin delivery therapy based on a patient-specific physiological simulator referred to herein as a "digital twin." Thus, the insulin delivery therapy can be determined in a manner that accounts for various idiosyncrasies of patient 12. More specifically, the digital twin may be a digital representation or replica that is based on a mathematical model having one or more patient-specific parameters (e.g., insulin sensitivity factor, body weight, insulin-to-carbohydrate ratio, endogenous glucose production, speed of carbohydrate absorption, and/or speed of insulin absorption). The digital twin may be implemented via software executing on one or more processors. The digital twin can simulate the interrelationship among meal content information, insulin dosage information, and glucose levels. For example, based on input comprising an estimated amount of carbohydrates a patient is to eat and a proposed amount of insulin to deliver to the patient, the digital twin may output information about what the glucose level of patient 12 may be for a postprandial period of time.

However, a digital twin may not be readily available for some patients. For example, a digital twin may not exist for a patient without an insulin therapy history, because generating a digital twin may involve deriving one or more patient-specific parameters based on the patient's physiological response to insulin.

This disclosure describes example techniques to determine an insulin delivery therapy even for such patients. More specifically, the example techniques involve determining an insulin delivery therapy for a current patient (e.g., patient 12) based on the digital twins of other patients.

For example, each digital twin may be used to simulate glucose levels resulting from each insulin delivery therapy of a plurality of insulin delivery therapies. Thus, for each of the other patients, an insulin delivery therapy may be selected from the plurality of insulin delivery therapies based on the simulations. The selected therapy may correspond to the best clinical outcome (e.g., comparatively greatest amount of time-in-range) for that patient. Based on the selected therapies for the other patients, a machine learning model may be generated to correlate insulin delivery therapies with patient characteristics (e.g., demographic information). This machine learning model may be applied to characteristics of the current patient to determine an insulin delivery therapy that corresponds to the best clinical outcome for the current patient.

In some examples, the determined insulin delivery therapy may be a "profile" of an insulin delivery therapy in that it includes general information about the therapy but excludes specific information that can vary from patient to patient. For example, a therapy profile may indicate whether patient 12 should receive the same amount of insulin after each meal and/or activity, customized (e.g., different) amounts of insulin after each meal and/or activity, customized amounts of insulin based on day of week, location, or time of day, and the like; however, the therapy profile may not specify any particular amount of insulin. Instead, a physician may select the specific amounts of insulin for the profile of insulin delivery therapy. In some examples, the determined insulin delivery therapy may include a profile of insulin delivery therapy as well as information indicating the amount of insulin to deliver after each meal and/or activity for physician review and approval.

As illustrated in FIG. 1, system 10A includes cloud 26 that includes one or more processors 28, database 30, digital representations 32, and optionally machine-learning (ML) model 34. As described in more detail below, one or more processors 28 may be configured to generate ML model 34 based on digital representations 32 and database 30. One or more processors 28, physician device 36, and/or patient device 24 may then utilize ML model 34 to determine insulin delivery therapy for patient 12.

Cloud 26 may include a plurality of network devices (e.g., servers), and each network device may include one or more processors. One or more processors 28 may be distributed across the plurality of network devices or may be located within a single one of the network devices. Cloud 26 represents a computing infrastructure that supports one or more processors 28 which may execute applications or operations requested by one or more users. For example, one or more processors 28 may remotely store, manage, and/or process data that would otherwise be locally stored, managed, and/or processed by patient device 24. One or more processors 28 may share data or resources for performing computations and may be part of computing servers, web servers, database servers, and the like. One or more processors 28 may be in network devices (e.g., servers) within a data center or may be distributed across multiple data centers. In some cases, the data centers may be in different geographical locations.

One or more processors 28, as well as other processing circuitry described herein, can include one or more of any of the following: microprocessors, digital signal processors (DSPs), application specific integrated circuits (ASICs), field programmable gate arrays (FPGAs), or any other equivalent integrated or discrete logic circuitry, as well as any combinations of such components. The functions attributed to one or more processors 28, as well as other processing circuitry described herein may be embodied as hardware, firmware, software, or any combination thereof.

One or more processors 28 may be implemented as fixed-function circuits, programmable circuits, or a combination thereof. Fixed-function circuits refer to circuits that provide particular functionality and are preset on the operations that can be performed. Programmable circuits refer to circuits that can be programmed to perform various tasks and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, one or more processors 28 may include distinct circuit blocks (fixed-function or programmable), and in some examples, one or more processors 28 may include integrated circuits. One or more processors 28 may include arithmetic logic units (ALUs), elementary function units (EFUs), digital circuits, analog circuits, and/or programmable cores, formed from programmable circuits. In examples where the operations of one or more processors 28 are performed using software executed by the programmable circuits, memory (e.g., on servers in cloud 26) accessible by one or more processors 28 may store the object code of the software that one or more processors 28 receive and execute.

Database 30 may maintain information for a plurality of patients (e.g., patients that are currently undergoing treatment for diabetes with delivery of insulin). The information for the plurality of patients may include information such as demographic information (e.g., age, weight, height, smoker or not, blood pressure, etc.) and information indicative of outcomes from therapies for the plurality of patients (e.g., how long does the glucose level stay within a target range for the patients, how many hypoglycemia events do the patients experience, what is the maximum glucose level, etc.). The information indicative of outcomes maintained on database 30 may include information of the results from the therapies that the patients are receiving. Database 30 may optionally maintain the profiles of the actual therapies that the patients are receiving.

For example, each patient of the plurality of patients may wear or may be attached with a respective monitoring device, like monitoring device 20. The glucose level measurements for each patient of the plurality of patients may be uploaded (e.g., via a respective patient device) to database 30. One or more processors 28 may access database 30 to determine the outcomes from the insulin delivery therapies that the plurality of patients are receiving. Although possible, it may not be necessary for database 30 to maintain, or for one or more processors 28 to utilize, the actual insulin delivery therapies that the plurality of patients are receiving.

As illustrated, cloud 26 may also include digital representations 32. Digital representations 32 may be digital replicas (e.g., digital twins) of the plurality of patients. Digital representations 32 may have been generated for determining insulin delivery therapies for the plurality of patients. As described in more detail, one or more processors 28 may leverage digital representations 32 of other patients for determining ML model 34 for determining insulin delivery therapy for the current patient 12.

Digital representations 32 are shown inside cloud 26 for ease of illustration. In some examples, digital representations 32 may be implemented via software executing on one or more processors 28. In some examples, the patient-specific parameters utilized by digital representations 32 may be maintained in database 30.

In accordance with one or more examples described in this disclosure, database 30 may maintain a plurality of insulin delivery therapies. Each insulin delivery therapy may define information such as whether the amount of insulin to deliver is the same for each delivery of insulin (e.g., a uniform bolus), whether the amount of insulin to deliver differs based on meal type (e.g., a bolus customized for breakfast, lunch, and dinner), whether the amount of insulin to deliver is different for different days of the week (e.g., a bolus customized for weekdays and weekends), and the like. In some examples, the insulin delivery therapies maintained in database 30 may include information indicative of the amount of insulin to deliver, but inclusion of the amount of insulin to deliver is not needed. In some examples, the insulin delivery therapies maintained in database 30 may include information such as amounts of insulin to deliver based on proximity to particular types of stores, restaurants, and the like.

Table 1 below provides an example of the plurality of insulin delivery therapies that database 30 may maintain. In some examples, each insulin delivery therapy may be a "balanced" therapy in that it seeks a balance between clinical outcome and patient adherence.

TABLE 1

| 1 | 2 | 3 | 4 | 5 | ... |
|---|---|---|---|---|---|
| Uniform bolus | Customized bolus for breakfast, lunch, dinner | Customized bolus for weekday, weekend | Customized bolus for menstrual cycle | Customized bolus for activity intensity | |

In one or more examples, one or more processors 28 may utilize digital representations 32 to simulate the physiological responses of the plurality of patients to receiving therapy in accordance with each insulin delivery therapy of the plurality of insulin delivery therapies. Thus, one or more processors 28 may generate a plurality of simulated therapy outcomes based on simulating, for each patient of the plurality of patients, a therapy outcome for each insulin delivery therapy of the plurality of insulin delivery therapies.

For each patient of the plurality of patients, one or more processors 28 may select an insulin delivery therapy from the plurality of insulin delivery therapies based on the plurality of simulated therapy outcomes. For example, one or more processors 28 may select the insulin delivery therapy that resulted in the best simulated therapy outcome (e.g., longest time in range, fewest hypoglycemia events, lowest maximum glucose level, etc.).

One or more processors 28 may provide the selected insulin delivery therapies to database 30. For each patient, database 30 may maintain a respective selected insulin delivery therapy in association with demographic information and/or information indicative of therapy outcomes. Table 2 is an example database table.

the generation of ML model 34, one or more processors 28 may update weights of ML model 34 such that for a given input, the output from ML model 34 is approximately equal to the ground truth.

One example of unsupervised training is k-means clustering, but other techniques for unsupervised training to generate ML model 34 are possible. For example, one or more processors 28 may utilize the information in Table 2 to generate clusters, where each cluster is determined based on demographic information, information indicative of outcomes from therapies, and selected insulin delivery therapies. The resulting organization of clusters may be an example of ML model 34.

In some examples, once ML model 34 is generated, ML model 34 may be repeatedly used for different patients to determine insulin delivery therapy. One or more processors 28 may update ML model 34 periodically using operations similar to those described above. For example, if there are any changes to the plurality of patients (e.g., one or more patients are added and/or removed) and/or the plurality of insulin delivery therapies (e.g., one or more insulin delivery therapies are added and/or removed), then one or more processors 28 may update ML model 34.

As illustrated in FIG. 1, physician device 36 and/or patient device 24 may access ML model 34 to determine an insulin delivery therapy for patient 12. For example, when a physician determines that patient 12 (e.g., a current patient) is to receive insulin therapy, physician device 36 may obtain patient characteristic information for patient 12. The patient characteristic information may be the demographic information of patient 12 and/or the desired outcome from therapy. For example, a user (e.g., the physician, physician's assistant, or nurse) may enter, into physician device 36, the age of patient 12, gender of patient 12, weight of patient 12, height of patient 12, whether patient 12 is a smoker or not, desired time-in-range, maximum allowable number of hypoglycemia events, maximum allowable glucose level, etc. Physician device 36 may communicate the patient characteristic information (e.g., the demographic information and/or the desired therapy outcome) to one or more processors 28, which may apply ML model 34 to the patient characteristic information to determine an insulin delivery therapy for recommendation to patient 12. One or more processors

TABLE 2

| | | | | | | Outcomes from therapy | | | |
|---|---|---|---|---|---|---|---|---|---|
| | | Demographic Information | | | | Time in | # Hypo- | Max Glucose level | Selected |
| Patient | Age | Gender | Weight | Height | Smoker? | Range | glycemia | (dl/mg) | therapy |
| 1 | 30 | Male | 185 | 6 ft | No | 80% | 0 | 110 | 2 |
| 2 | 45 | Male | 250 | 6 ft 1 in | Yes | 75% | 2 | 180 | 19 |
| 3 | 25 | Female | 200 | 5 ft 5 in | No | 90% | 4 | 145 | 8 |
| 4 | 65 | Female | 140 | 5 ft 3 in | No | 80% | 0 | 175 | 15 |
| ... | ... | ... | ... | ... | ... | ... | ... | ... | ... |

One or more processors 28 may generate ML model 34 based on the demographic information, information indicative of outcomes from therapies, and selected insulin delivery therapies. For example, one or more processors 28 may generate ML model 34 based on supervised training or unsupervised training.

For supervised training, Table 2 may be the "ground truth" used to generate ML model 34. For example, during

28 may communicate data indicative of the insulin delivery therapy to physician device 36 for presentation to the physician.

In some examples, the physician may review and evaluate the insulin delivery therapy to determine whether the insulin delivery therapy is appropriate for patient 12. In some examples, the physician may also determine one or more insulin amounts for the insulin delivery therapy. For instance, the insulin delivery therapy may specify different amounts of insulin on weekdays and weekends (e.g., dosages on weekdays are different than dosages on weekends), and the physician may specify the different amounts of insulin. However, in some other examples, the insulin delivery therapy may include a recommendation of the one or more amounts of insulin for physician review.

Upon physician approval, insulin pump 14 may be configured to deliver insulin in accordance with the insulin delivery therapy. This may be achieved in a variety of ways. For example, insulin pump 14 may be communicatively coupled to physician device 26, which may automatically configure insulin pump 14. As another example, physician device 26 may communicate data indicative of the approval to cloud 16, which communicates data indicative of the insulin delivery therapy to patient device 24. In some examples, patient device 24 may automatically configure insulin pump 14 accordingly.

In some examples, determination of the insulin delivery therapy for patient 12 may be performed multiple times. For example, if the physician determines that a first insulin delivery therapy is resulting in an unsatisfactory clinical outcome (e.g., because patient 12 is not sufficiently adhering to the first insulin delivery therapy), the aforementioned techniques may be repeated to determine a second insulin delivery therapy for patient 12. Other example reasons for repeating the determination of insulin delivery therapy include a change in the demographics of patient 12 (e.g., gain or loss of weight, quitting smoking, increase in age, etc.) and/or the desired outcome from therapy (e.g., longer or short time in range, higher or lower maximum glucose level, etc.).

Although the above examples describe machine learning techniques implemented in cloud 26, it should be appreciated that implementations of the machine learning techniques are not limited to cloud 26. For example, the machine learning techniques may be implemented in a distributed manner involving cloud 26, physician device 36, and/or patient device 24. Thus, one or more processors 28, one or more processors of physician device 36, and/or one or more processors of patient device 24 may be configured to perform the example techniques described in this disclosure based on executing instructions stored in one or more processor-readable storage media (e.g., a memory of a network device in cloud 26, a memory of physician device 36, and/or a memory of patient device 24).

Figure 2:
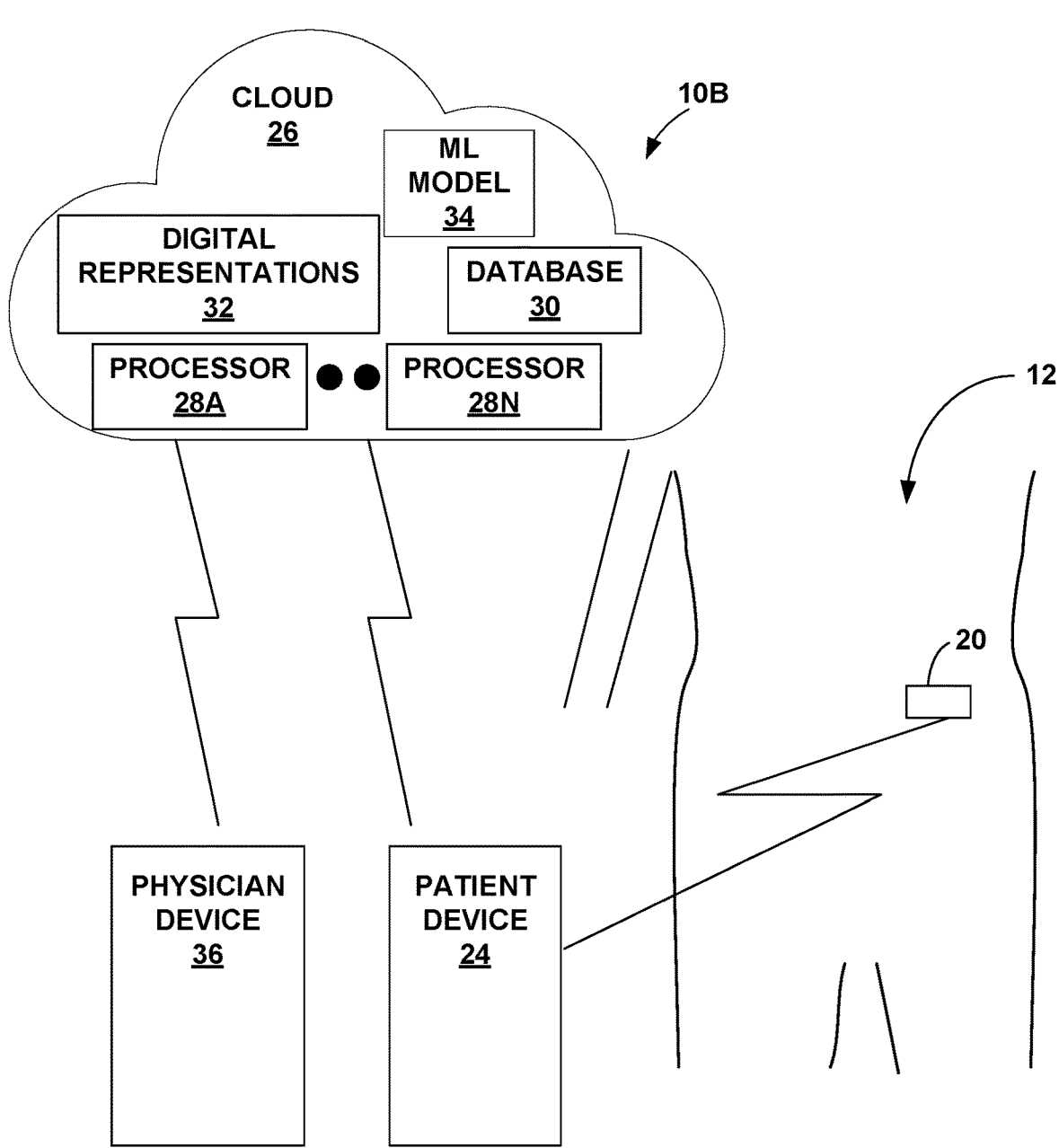
FIG. 2 is a block diagram illustrating an example insulin therapy determination system comprising a manual injection device, in accordance with one or more examples described in this disclosure.

FIG. 2 is a block diagram illustrating an example insulin therapy determination system comprising a manual injection device (not shown), in accordance with one or more examples described in this disclosure. FIG. 2 illustrates system 10B, which is similar to system 10A of FIG. 1. However, in system 10B, patient 12 may not have insulin pump 14. Rather, patient 12 may utilize a manual injection device (e.g., an insulin pen or a syringe) to deliver insulin. For example, rather than insulin pump 14 automatically delivering insulin, patient 12 (or a caretaker of patient 12) may fill a syringe with insulin, set the dosage amount in an insulin pen, and perform an injection.

The example of system 10B may operate in substantially the same manner as the example of system 10A. However, in system 10B, there is no insulin pump 14 to configure. Thus, upon obtaining physician approval, cloud 26 may communicate information indicative of the determined insulin delivery therapy to patient device 24, which may periodically present information to patient 12 or a caretaker of patient 12 for filling a syringe or insulin pen with an appropriate amount of insulin for delivery.

Figure 3:
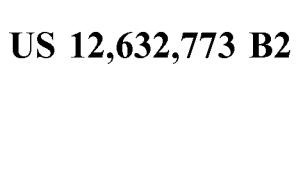
FIG. 3 is a block diagram illustrating an example insulin therapy determination system comprising a networked injection device, in accordance with one or more examples described in this disclosure.

FIG. 3 is a block diagram illustrating another example insulin therapy determination system comprising a networked injection device, in accordance with one or more examples described in this disclosure. FIG. 3 illustrates system 10C, which is similar to system 10A of FIG. 1 and system 10B of FIG. 2. In system 10C, patient 12 may not have insulin pump 14. Rather, patient 12 may utilize injection device 40 to deliver insulin. For example, rather than insulin pump 14 automatically delivering insulin, patient 12 (or a caretaker of patient 12) may utilize injection device 40 to perform an injection.

Injection device 40 may be different than a syringe because injection device 40 may be a device that can communicate with patient device 24, physician device 36, and/or other devices in system 10C. For example, injection device 40 may receive information indicative of the determined insulin delivery therapy and may automatically set the appropriate amounts of insulin for delivery to patient 12 in accordance with the determined insulin delivery therapy.

Also, injection device 40 may include a reservoir and, based on information indicative of how much therapy dosage to deliver, may be able to dose out that much insulin for delivery. For example, injection device 40 may automatically set the amount of insulin based on the information received from patient device 24 and/or physician device 36. In some examples, injection device 40 may be similar to insulin pump 14 but not worn by patient 12. One example of injection device 40 is an insulin pen, sometimes also called a smart insulin pen. Another example of injection device 40 may be an insulin pen with a smart cap, where the smart cap can be used to set particular doses of insulin.

The above examples describe insulin pump 14, a syringe, and injection device 40 as example ways in which to deliver insulin. In this disclosure, the term "insulin delivery device" may generally refer to any device used to deliver insulin. Examples of insulin delivery device include insulin pump 14, a syringe, and injection device 40. As described, the syringe may be a device used to inject insulin but is not necessarily capable of communicating or dosing a particular amount of insulin. Injection device 40, however, may be a device used to inject insulin that may be capable of communicating with other devices (e.g., via Bluetooth, BLE, and/or Wi-Fi) or may be capable of dosing a particular amount of insulin. Injection device 40 may be a powered (e.g., battery-powered) device, and the syringe may be a device that requires no power.

Figure 4:
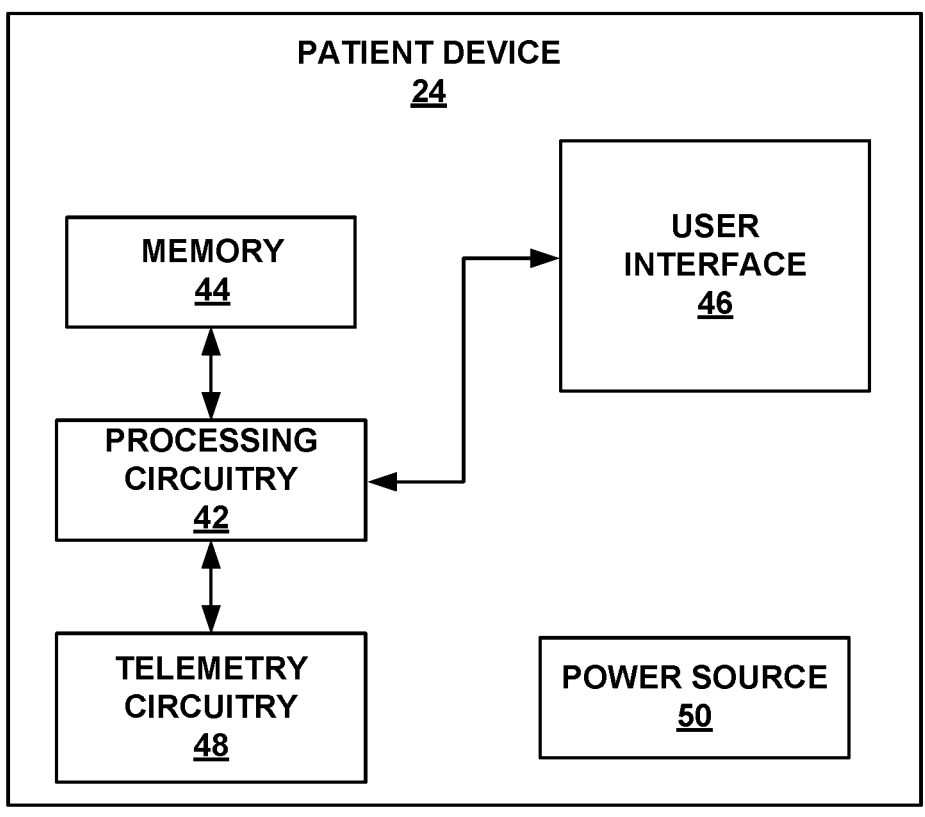
FIG. 4 is a block diagram illustrating an example of a patient device, in accordance with one or more examples described in this disclosure.

FIG. 4 is a block diagram illustrating an example of a patient device, in accordance with one or more examples described in this disclosure. While patient device 24 may generally be described as a hand-held computing device, in some examples, patient device 24 may be a notebook computer or a workstation, for example. In some examples, patient device 24 may be a mobile device, such as a smartphone or a tablet computer. Patient device 24 may execute an application that allows patient device 24 to perform example techniques described in this disclosure. In some examples, patient device 24 may be a specialized controller for communicating with insulin pump 14.

As illustrated in FIG. 4, patient device 24 may include processing circuitry 42, memory 44, user interface 46, telemetry circuitry 48, and power source 50. Memory 44 may store program instructions that, when executed by processing circuitry 42, cause processing circuitry 42 to provide the functionality ascribed to patient device 24 throughout this disclosure. For example, memory 44 is an example of one or more processor-readable storage media storing instructions which, when executed by processing circuitry 42, cause performance of one or more example techniques described in this disclosure.

In some examples, memory 44 of patient device 24 may store a plurality of parameters, such as amounts of insulin to deliver, target glucose level, time of delivery, etc. Processing circuitry 42 (e.g., through telemetry circuitry 48) may output the parameters stored in memory 44 to insulin pump 14 or injection device 40 for delivery of insulin to patient 12. In some examples, processing circuitry 42 may execute a notification application, stored in memory 44, that outputs notifications to patient 12, such as a notification to take insulin, amount of insulin, and time to take the insulin, via user interface 46.

Memory 44 may include any volatile, non-volatile, fixed, removable, magnetic, optical, or electrical media, such as RAM, ROM, hard disk, removable magnetic disk, memory cards or sticks, NVRAM, EEPROM, flash memory, and the like. Processing circuitry 42 can take the form one or more microprocessors, DSPs, ASICs, FPGAs, programmable logic circuitry, or the like, and the functions attributed to processing circuitry 42 herein may be embodied as hardware, firmware, software or any combination thereof.

User interface 46 may include a button or keypad, lights, a microphone for voice commands, and/or a display device, such as a liquid crystal (LCD). In some examples the display may be a touchscreen. As discussed in this disclosure, processing circuitry 42 may present and receive information relating to therapy via user interface 46. For example, processing circuitry 42 may receive patient input via user interface 46. The patient input may be entered, for example, by pressing a button on a keypad, entering text via the keypad, or selecting an icon from a touchscreen.

Telemetry circuitry 48 includes any suitable hardware, firmware, software, or any combination thereof for communicating with another device, such as a device in cloud 26, physician device 36, insulin pump 14 or injection device 40, as applicable, and monitoring device 20. Telemetry circuitry 48 may receive communication with the aid of an antenna, which may be internal and/or external to patient device 24. Telemetry circuitry 48 may be configured to communicate with another computing device via wireless communication techniques or direct communication through a wired connection. Examples of local wireless communication techniques that may be employed to facilitate communication between patient device 24 and another computing device include RF communication according to IEEE 802.11, Bluetooth, or BLE specification sets, infrared communication, e.g., according to an IrDA standard, or other standard or proprietary telemetry protocols. Telemetry circuitry 48 may also provide connection with carrier network for access to cloud 26. In this manner, other devices may be capable of communicating with patient device 24.

Power source 50 delivers operating power to the components of patient device 24. In some examples, power source 50 may include a battery, such as a rechargeable or non-rechargeable battery. A non-rechargeable battery may last for several months or years, while a rechargeable battery may be periodically charged from an external device, e.g., on a daily or weekly basis. Recharging of a rechargeable battery may be accomplished by using an alternating current (AC) outlet or through proximal inductive interaction between an external charger and an inductive charging coil within patient device 24.

Figure 5:
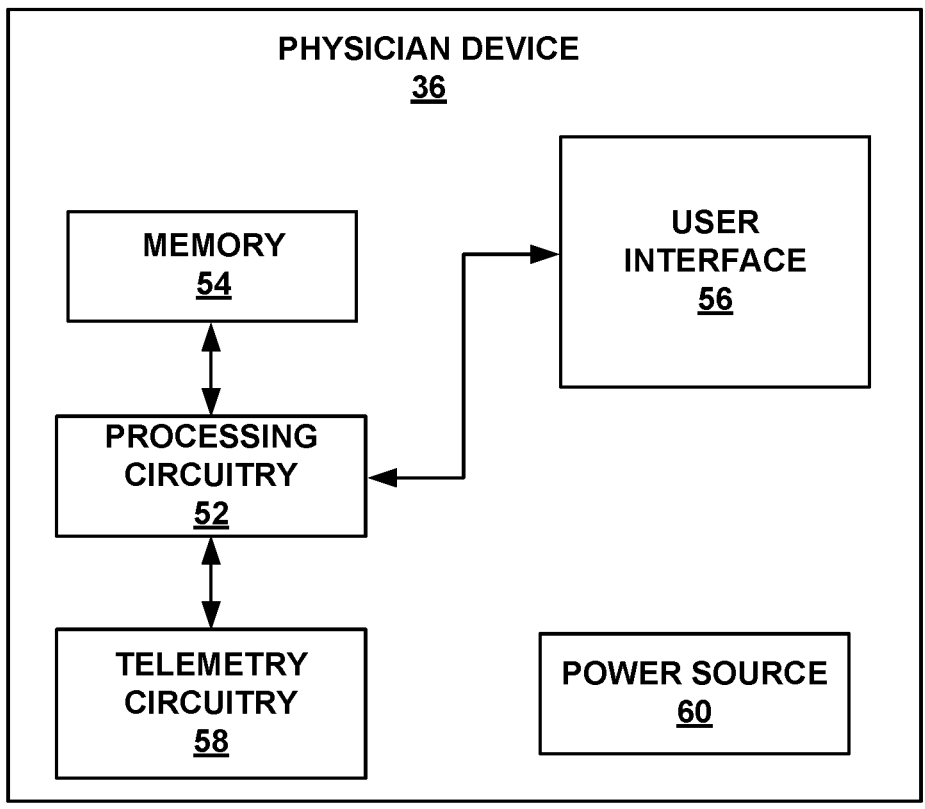
FIG. 5 is a block diagram illustrating an example of a physician device, in accordance with one or more examples described in this disclosure.

FIG. 5 is a block diagram illustrating an example of a physician device, in accordance with one or more examples described in this disclosure. Physician device 36 may be similar to patient device 24. However, in some examples, physician device 36 may be a laptop, desktop, notebook computer, or a workstation.

Memory 54 may be similar to memory 44 of FIG. 4, processing circuitry 52 may be similar to processing circuitry 42 of FIG. 4, telemetry circuitry 58 may be similar to telemetry circuitry 48 of FIG. 4, and user interface 56 may be similar to user interface 46 of FIG. 4. In examples where physician device 36 is a desktop or workstation, power source 60 may include an AC/DC converter that plugs into a wall socket for electricity. In examples where physician device 36 is a laptop or handheld device, power source 60 may be similar to power source 50 of FIG. 4.

Figure 6:
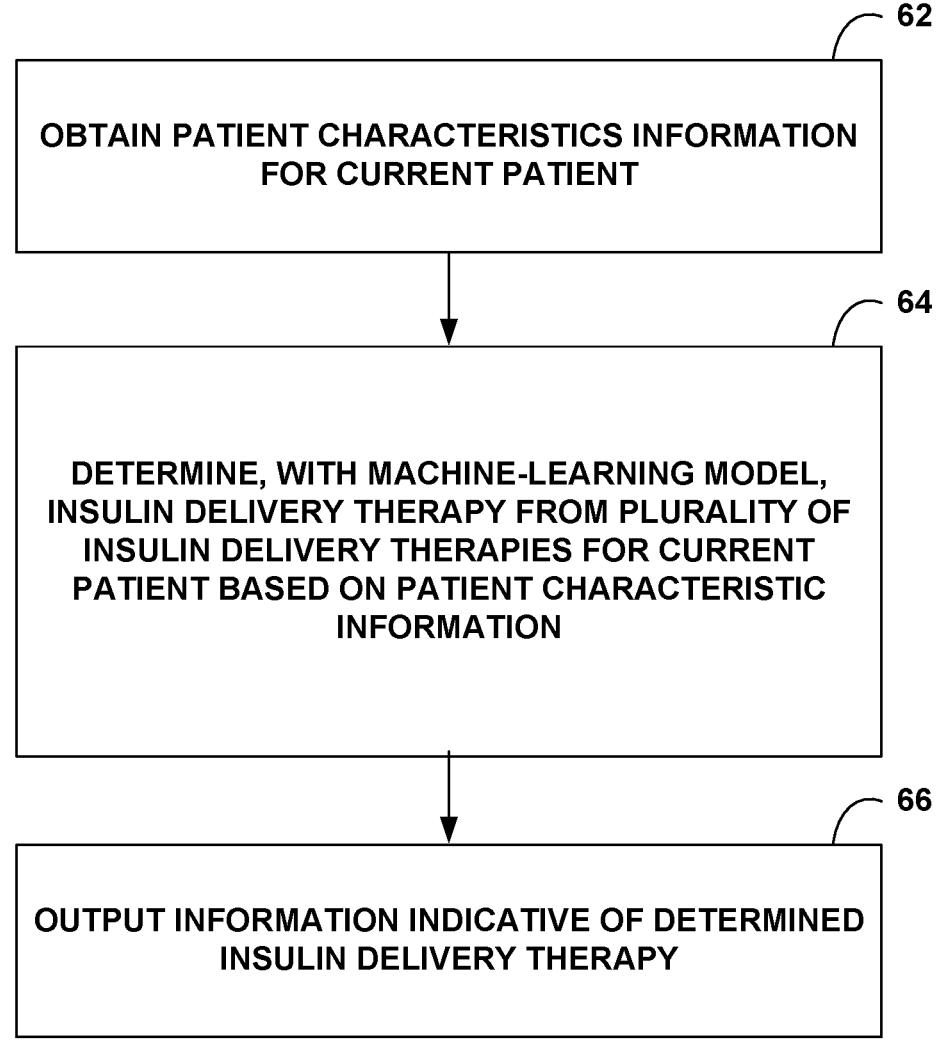
FIG. 6 is a flowchart illustrating an example process for insulin therapy determination.

FIG. 6 is a flowchart illustrating an example process for insulin therapy determination. For purposes of illustration, the example process of FIG. 6 is described with respect to one or more processors, and one or more processor-readable storage media storing instructions which, when executed by the one or more processors, cause performance of the example techniques described in FIG. 6. Examples of the one or more processors include one or more processors 28, one or more processors of processing circuitry 42, and/or one or more processors of processing circuitry 52. Examples of the one or more processor-readable storage media include one or more memories of one or more devices in cloud 26; memory 44; and/or memory 54.

The one or more processors may obtain patient characteristics information for a current patient 12 (62). Examples of the patient characteristics include demographic information for patient 12 (e.g., height, weight, gender, whether a smoker, etc.) and/or desired outcome of therapy (e.g., desired time in range, maximum allowable number of hypoglycemia events, maximum allowable glucose level, etc.). The one or more processors may obtain the patient characteristics information from patient device 24 and/or physician device 36, which may obtain at least some of the patient characteristics information through user interface 46 and/or user interface 56.

The one or more processors may determine, with a machine-learning model (e.g. ML model 34), an insulin delivery therapy from a plurality of insulin delivery therapies for the current patient 12 based on the patient characteristics information (64). In some examples, each insulin delivery therapy of the plurality of insulin delivery therapies may represent a different balance between the likelihood of patient adherence to the therapy and the clinical outcome of the therapy. For example, a first therapy specifying a uniform bolus amount may place a greater weight on patient adherence than on clinical outcome, whereas a second therapy specifying different bolus amounts may place a greater weight on clinical outcome than on patient adherence. However, due to the patient adherence factor, the first therapy may provide the best therapy outcome for some patients, and the second therapy may provide the best therapy outcome for some other patients. Based on the assumption that patient characteristics can be used to predict patient adherence, ML model 34 may correlate patient characteristics with therapies predicted to provide the best outcome for patients with those characteristics.

As will be described in greater detail with reference to FIG. 7, the machine-learning model (e.g., ML model 34) may be generated based on digital representations 32 of a plurality of patients. In some examples, the plurality of patients may exclude the current patient 12. Thus, the one or more processors may be able to determine the insulin delivery therapy without utilizing a digital representation for the current patient 12 (e.g., no digital twin for current patient 12 is needed).

The one or more processors may output information indicative of the insulin delivery therapy that is determined at block 64 (66). For example, the one or more processors may output the information indicative of the determined insulin delivery therapy to physician device 36 for display. The physician may review and approve the determined insulin delivery therapy. In some examples, the information indicative of the determined insulin delivery therapy may include a profile of the insulin delivery therapy and may not include information indicative of the amounts of insulin to deliver. In such examples, the physician may recommend the amounts of insulin to deliver.

The example process of FIG. 6 may be repeated (e.g., periodically, when there are any changes in the demographic information of patient 12, and/or when there are any changes in the desired outcome of therapy). In some examples, after the initial determination of the insulin delivery therapy, patient 12 may receive therapy in accordance with the insulin delivery therapy. During this time, it may be possible to capture the actual outcome from the insulin delivery therapy. If the actual outcome (e.g., time-in-range) from the insulin delivery therapy is not satisfactory, the physician may change the desired outcome from therapy.

In some examples, the patient characteristics information for the current patient 12 used in the example process of FIG. 6 may be considered as a first instance of patient characteristics information for the current patient 12, and the insulin delivery therapy may be considered as a first instance of insulin delivery therapy. The one or more processors may be configured to obtain a second instance of patient characteristics information for the current patient at an amount of time (e.g., 3 months or 6 months) after obtaining the first instance of patient characteristics information. The one or more processors may determine, with the machine-learning model (e.g., ML model 34), a second instance of insulin delivery therapy from the plurality of insulin delivery therapies for the current patient 12, based on the second instance of patient characteristics information, and output information indicative of the determined second instance of insulin delivery therapy.

FIG. 7 is a flowchart illustrating an example process for generating a machine learning model for insulin therapy determination. For purposes of illustration, the example process of FIG. 7 is described with respect to one or more processors and one or more processor-readable storage media storing instructions which, when executed by the one or more processors, cause performance of the example techniques described in FIG. 7. Examples of the one or more processors include one or more processors 28, one or more processors of processing circuitry 42, and/or one or more processors of processing circuitry 52. Examples of the one or more processor-readable storage media include memory 44, memory 54, and/or one or more memories of one or more devices in cloud 26.

For example, the one or more processors may include a first set of processors and a second set of processors, and the one or more processor-readable storage media may comprise a first set of processor-readable storage media and a second set of processor-readable storage media. Patient device 24 and/or physician device 36 may include the first set of processors and the first set of processor-readable storage media. One or more devices in cloud 26 may include the second set of processors (e.g., one or more processors 28) and the second set of processor-readable storage media.

One or more processors 28 may obtain, for each patient of a plurality of patients, demographic information and information indicative of outcomes from therapy (72). The plurality of patients may exclude patient 12. The outcomes from therapy may be maintained in database 30 (e.g., based on measurements from monitoring devices on the plurality of patients). Database 30 may also maintain demographic information for each patient of the plurality of patients.

One or more processors 28 may simulate, for each patient of the plurality of patients, using a respective digital representation, therapy outcomes for each insulin delivery therapy of the plurality of insulin delivery therapies to generate a plurality of simulated therapy outcomes (74). For example, there may be at least 5000 patients (e.g., 10,000 patients) and at least 5 insulin delivery therapies (e.g., 20). For a first patient, one or more processors 28 may generate twenty simulated therapy outcomes (e.g., one for each of the twenty insulin delivery therapies). For a second patient, one or more processors 28 may generate twenty simulated therapy outcomes, and so forth for each of the (e.g., 10,000) patients.

In one or more examples, one or more processors 28 may select, for each patient of the plurality of patients, a respective insulin delivery therapy from the plurality of insulin delivery therapies based on the plurality of simulated therapy outcomes (76). For example, one or more processors 28 may determine, for the first patient of the 10,000 patients, which of the twenty simulated therapy outcome is the best and select the insulin delivery therapy that resulted in the best outcome. For the second patient of the 10,000 patients, one or more processors 28 may determine which of the twenty simulated therapy outcomes is the best and select the insulin delivery therapy that resulted in the best outcome, and so forth. The selections may be maintained in a database table like Table 2, where each patient's demographic information is maintained in association with outcomes from therapy and a selected insulin delivery therapy.

One or more processors 28 may generate the machine-learning model (e.g., ML model 34) based on the demographic information, information indicative of outcomes from therapy, and selected insulin delivery therapy of each patient of the plurality of patients (78). As one example, ML model 34 may be generated using supervised training. For instance, the example of Table 2 may be the ground truth that is used to generate ML model 34. As another example, ML model 34 may be generated using unsupervised training. For instance, one or more processors 28 may utilize k-means clustering to form clusters of patients having similar characteristics based on the example of Table 2.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media or processor-readable storage media may include computer-readable storage media or processor-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including one or more processors 28 of cloud 26, one or more processors of patient device 24, one or more processors of wearable device 22, one or more processors of insulin pump 14, or some combination thereof. The one or more processors may be one or more integrated circuits (ICs), and/or discrete electrical circuitry, residing in various locations in the example systems described in this disclosure.

The one or more processors or processing circuitry utilized for example techniques described in this disclosure may be implemented as fixed-function circuits, programmable circuits, or a combination thereof. Fixed-function circuits refer to circuits that provide particular functionality, and are preset on the operations that can be performed. Programmable circuits refer to circuits that can be programmed to perform various tasks, and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits. The processors or processing circuitry may include arithmetic logic units (ALUs), elementary function units (EFUs), digital circuits, analog circuits, and/or programmable cores, formed from programmable circuits. In examples where the operations of the processors or processing circuitry are performed using software executed by the programmable circuits, memory accessible by the processors or processing circuitry may store the object code of the software that the processors or processing circuitry receive and execute.

Various aspects of the disclosure have been described. These and other aspects are within the scope of the following claims.

What is claimed is:

1. A system for determining insulin therapy, the system comprising:

one or more processors; and one or more processor-readable storage media storing instructions which, when executed by the one or more processors, cause performance of:

obtaining patient characteristic information and one or more target therapy efficacy metrics representative of a desired clinical outcome for a current patient, wherein the one or more target therapy efficacy metrics include a target time spent within a target range having an upper limit and a lower limit;

determining, based on an output of a machine-learning model that takes the patient characteristic information and the one or more target therapy efficacy metrics as an input, an insulin delivery therapy from a plurality of insulin delivery therapies for the current patient by selecting between an insulin delivery therapy that delivers the same amount of insulin for each meal, and an insulin delivery therapy that customizes insulin amounts, wherein the machine-learning model has been trained to determine whether an insulin therapy that customizes insulin amounts for each meal or delivers the same amount of insulin for each meal will cause the current patient to achieve the desired clinical outcome represented in the one or more target therapy efficacy metrics based on the current patient having the patient characteristic information;

outputting information indicative of the determined insulin delivery therapy; and delivering insulin, using an insulin pump, to the current patient in accordance with the determined insulin delivery therapy, wherein delivering the insulin causes a glucose level of the patient to decrease to within the target range.

2. The system of claim 1, wherein the plurality of insulin delivery therapies comprises at least a first insulin delivery therapy indicating the same amount of insulin for each meal, a second insulin delivery therapy indicating customized insulin amounts for each meal, and a third insulin delivery therapy indicating a first insulin amount for meals during a first set of days and a second insulin amount for meals during a second set of days.

3. The system of claim 1, wherein the patient characteristic information for the current patient comprises a first instance of patient characteristic information for the current patient, wherein the determined insulin delivery therapy comprises a first instance of insulin delivery therapy, and wherein the one or more processor-readable storage media further store instructions which, when executed by the one or more processors, cause performance of:

obtaining a second instance of patient characteristic information for the current patient after obtaining the first instance of patient characteristic information;

determining, with the machine-learning model, a second instance of insulin delivery therapy from the plurality of insulin delivery therapies for the current patient based on the second instance of patient characteristic information;

outputting information indicative of the determined second instance of insulin delivery therapy.

4. The system of claim 1, wherein the one or more processor-readable storage media further store instructions which, when executed by the one or more processors, cause performance of:

obtaining, for each patient of a plurality of patients, demographic information and information indicative of outcomes from therapy;

simulating, for each patient of the plurality of patients, using a respective digital representation, therapy outcomes for each insulin delivery therapy of the plurality of insulin delivery therapies to generate a plurality of simulated therapy outcomes;

selecting, for each patient of the plurality of patients, a respective insulin delivery therapy from the plurality of insulin delivery therapies based on the plurality of simulated therapy outcomes, wherein the selected respective insulin delivery therapy corresponds to an insulin delivery therapy associated with a best simulated therapy outcome of the plurality of simulated therapy outcomes; and generating the machine-learning model based on the demographic information, information indicative of outcomes from therapy, and selected insulin delivery therapy of each patient of the plurality of patients.

5. The system of claim 1, wherein the machine-learning model is generated based on supervised training.

6. The system of claim 1, wherein generating the machine-learning model comprises generating a plurality of clusters, each cluster corresponding to an insulin delivery therapy of the plurality of insulin delivery therapies, and wherein determining, based on the output of the machine-learning model, the insulin delivery therapy comprises assigning the current patient to a cluster of the plurality of clusters based on the patient characteristic information.

7. The system of claim 1, wherein determining the insulin delivery therapy from the plurality of insulin delivery therapies for the current patient comprises determining the insulin delivery therapy without utilizing a digital representation for the current patient.

8. A method for determining insulin therapy, the method comprising:

obtaining patient characteristic information and one or more target therapy efficacy metrics representative of a desired clinical outcome for a current patient, wherein the one or more target therapy efficacy metrics include a target time spent within a target range having an upper limit and a lower limit;

determining, based on an output of a machine-learning model that takes the patient characteristic information and the one or more target therapy efficacy metrics as an input, an insulin delivery therapy from a plurality of insulin delivery therapies for the current patient by selecting between an insulin delivery therapy that delivers the same amount of insulin for each meal, and an insulin delivery therapy that customizes insulin amounts, wherein:

the machine-learning model has been trained to determine whether an insulin therapy that customizes insulin amounts for each meal or delivers the same amount of insulin for each meal will cause the current patient to achieve the desired clinical outcome represented in the one or more target therapy efficacy metrics based on the current patient having the patient characteristic information;

outputting information indicative of the determined insulin delivery therapy; and delivering insulin, using an insulin pump, to the current patient in accordance with the determined insulin delivery therapy, wherein delivering the insulin causes a glucose level of the patient to decrease to within the target range.

9. The method of claim 8, wherein the plurality of insulin delivery therapies comprises at least a first insulin delivery therapy indicating the same amount of insulin for each meal, a second insulin delivery therapy indicating customized insulin amounts for each meal, and a third insulin delivery therapy indicating a first insulin amount for meals during a first set of days and a second insulin amount for meals during a second set of days.

10. The method of claim 8, wherein the patient characteristic information for the current patient comprises a first instance of patient characteristic information for the current patient, wherein the determined insulin delivery therapy comprises a first instance of insulin delivery therapy, and wherein the method further comprises:

obtaining a second instance of patient characteristic information for the current patient after obtaining the first instance of patient characteristic information;

determining, with the machine-learning model, a second instance of insulin delivery therapy from the plurality of insulin delivery therapies for the current patient based on the second instance of patient characteristic information;

outputting information indicative of the determined second instance of insulin delivery therapy.

11. The method of claim 8, further comprising:

obtaining, for each patient of a plurality of patients, demographic information and information indicative of outcomes from therapy;

simulating, for each patient of the plurality of patients, using a respective digital representation, therapy outcomes for each insulin delivery therapy of the plurality of insulin delivery therapies to generate a plurality of simulated therapy outcomes;

selecting, for each patient of the plurality of patients, a respective insulin delivery therapy from the plurality of insulin delivery therapies based on the plurality of simulated therapy outcomes; and generating the machine-learning model based on the demographic information, information indicative of outcomes from therapy, and selected insulin delivery therapy of each patient of the plurality of patients.

12. The method of claim 8, wherein the machine-learning model is generated based on supervised training.

13. The method of claim 8, wherein the machine-learning model is generated based on unsupervised training.

14. The method of claim 8, wherein determining the insulin delivery therapy from the plurality of insulin delivery therapies for the current patient comprises determining the insulin delivery therapy without utilizing a digital representation for the current patient.

15. One or more non-transitory processor-readable storage media storing instructions which, when executed by the one or more processors, cause performance of:

obtaining patient characteristic information and one or more target therapy efficacy metrics representative of a desired clinical outcome for a current patient, wherein the one or more target therapy efficacy metrics include a target time spent within a target range having an upper limit and a lower limit and a maximum allowable number of hypoglycemic events;

determining, based on an output of a machine-learning model that takes the patient characteristic information and the one or more target therapy efficacy metrics as an input, an insulin delivery therapy from a plurality of insulin delivery therapies for the current patient by selecting between an insulin delivery therapy that delivers the same amount of insulin for each meal, and an insulin delivery therapy that customizes insulin amounts, wherein:

the machine-learning model has been trained to determine whether an insulin delivery therapy that customizes insulin amounts for each meal or delivers the same amount of insulin for each meal will cause the current patient to achieve the desired clinical outcome represented in the one or more target therapy efficacy metrics based on the current patient having the patient characteristic information, and wherein the machine-learning model has been trained to account for an accuracy of the current patient in counting carbohydrates based on the patient characteristic information in the determination of the insulin delivery therapy;

outputting information indicative of the determined insulin delivery therapy; and delivering insulin, using an insulin pump, to the current patient in accordance with the determined insulin delivery therapy, wherein delivering the insulin causes a glucose level of the patient to decrease to within the target range.

16. The one or more non-transitory processor-readable storage media of claim 15, wherein the plurality of insulin delivery therapies comprises at least a first insulin delivery therapy indicating the same amount of insulin for each meal, a second insulin delivery therapy indicating customized insulin amounts for each meal, and a third insulin delivery therapy indicating a first insulin amount for meals during a first set of days and a second insulin amount for meals during a second set of days.

17. The one or more non-transitory processor-readable storage media of claim 15, wherein the patient characteristic information for the current patient comprises a first instance of patient characteristic information for the current patient, wherein the determined insulin delivery therapy comprises a first instance of insulin delivery therapy, and wherein the one or more non-transitory processor-readable storage media further store instructions which, when executed by the one or more processors, cause performance of:

obtaining a second instance of patient characteristic information for the current patient after obtaining the first instance of patient characteristic information;

determining, with the machine-learning model, a second instance of insulin delivery therapy from the plurality of insulin delivery therapies for the current patient based on the second instance of patient characteristic information;

outputting information indicative of the determined second instance of insulin delivery therapy.

18. The one or more non-transitory processor-readable storage media of claim 15, further storing instructions which, when executed by the one or more processors, cause performance of:

obtaining, for each patient of a plurality of patients, demographic information and information indicative of outcomes from therapy;

simulating, for each patient of the plurality of patients, using a respective digital representation, therapy outcomes for each insulin delivery therapy of the plurality of insulin delivery therapies to generate a plurality of simulated therapy outcomes;

selecting, for each patient of the plurality of patients, a respective insulin delivery therapy from the plurality of insulin delivery therapies based on the plurality of simulated therapy outcomes; and generating the machine-learning model based on the demographic information, information indicative of outcomes from therapy, and selected insulin delivery therapy of each patient of the plurality of patients.

19. The one or more non-transitory processor-readable storage media of claim 15, wherein the machine-learning model is generated based on supervised training.

20. The one or more non-transitory processor-readable storage media of claim 15, wherein determining the insulin delivery therapy from the plurality of insulin delivery therapies for the current patient comprises determining the insulin delivery therapy without utilizing a digital representation for the current patient.

* * * * *